(12) United States Patent
Willuhn et al.

(10) Patent No.: US 7,659,364 B2
(45) Date of Patent: Feb. 9, 2010

(54) N-METHYL-HOMOCYSTEINES AND THEIR USE AS WELL AS PROCESS FOR THEIR PRODUCTION

(75) Inventors: Marc Willuhn, Berlin (DE); Johannes Platzek, Berlin (DE); Eckhard Ottow, Berlin (DE); Orlin Petrov, Berlin (DE); Claudia Borm, Berlin (DE); Dirk Hinz, Berlin (DE); Gregor Mann, Berlin (DE); John Lister-James, Bedford, NH (US); David M. Wilson, Bow, NH (US)

(73) Assignee: CIS Bio International, Gif sur Yvette Cedex (FR)

( * ) Notice: Subject to any disclaimer, the term of this patent is extended or adjusted under 35 U.S.C. 154(b) by 1263 days.

(21) Appl. No.: 10/295,043

(22) Filed: Nov. 15, 2002

(65) Prior Publication Data

US 2003/0120032 A1  Jun. 26, 2003

Related U.S. Application Data

(60) Provisional application No. 60/331,416, filed on Nov. 15, 2001.

(30) Foreign Application Priority Data

Mar. 28, 2002  (DE) ................. 102 15 336

(51) Int. Cl.
*A61K 38/12* (2006.01)
*A61K 38/00* (2006.01)
*A61K 51/00* (2006.01)

(52) U.S. Cl. ............... 530/317; 514/2; 424/1.69

(58) Field of Classification Search ............. 530/317
See application file for complete search history.

(56) References Cited

U.S. PATENT DOCUMENTS

| 5,932,189 | A  | * | 8/1999  | Dean et al. ............. 424/1.69 |
| 6,333,410 | B1 |   | 12/2001 | Chari et al. |
| 6,358,491 | B1 | * | 3/2002  | Lister-James et al. ...... 424/1.69 |
| 6,841,559 | B1 | * | 1/2005  | Almqvist et al. ............ 514/301 |

FOREIGN PATENT DOCUMENTS

WO  WO 01 36426  *  5/2001

OTHER PUBLICATIONS

Wood et al. Conversion in vitro of the S-benzyl-N-methyl derivatives of cysteine and homocysteine to the N-acetyl-S-benzyl derivatives of cysteine and homocysteine. J. Biol. Chem. (1946), 165, 95-6 (abstract).*

R.M. Freidinger et al: "Synthesis of 9-Fluorenylmethydroxycarbonyl-Proctected N-Alkyl Amino Acids by Reduction of Oxazolidinones" Journal of Organic Chemistry, Bd. 48, 1983, Seiten 77-81, XP002235793 in der Anmeldung erwähnt das ganze Dokument.

* cited by examiner

*Primary Examiner*—Maury Audet
(74) *Attorney, Agent, or Firm*—Millen, White, Zelano & Branigan, P.C.

(57) ABSTRACT

The synthesis of N-methyl-homocysteines and their use are described.

17 Claims, No Drawings

N-METHYL-HOMOCYSTEINES AND THEIR USE AS WELL AS PROCESS FOR THEIR PRODUCTION

This application claims the benefit of the filing date of U.S. Provisional Application Ser. No. 60/331,416 filed Nov. 15, 2001.

The invention relates to the subjects that are characterized in the claims, namely N-methyl-homocysteines of general formulas I and II, their use, and process for their production.

N-Methyl-amino acids are valuable intermediate products in synthetic chemistry. Primarily pharmaceutical chemistry uses such components very frequently, since many highly potent and selective pharmaceutical agents contain N-methyl-amino acids.

Optically active N-methyl-amino acids occur naturally as single compounds (e.g., N-methyl-tryptophans; Liebigs Ann. Chem. 1935, 520, 31-34), but are also used as components in a number of biologically active natural substances, such as, e.g., the dolastatins (G. R. Pettit et al., J. Org. Chem. 1990, 55, 2989-2990; Tetrahedron 1993, 41, 9151-9170) or the didemnins (K. L. Rinehart et al., J. Nat. Prod. 1988, 51, 1-21; J. Am. Chem. Soc. 1987, 109, 6846-6848; J. Am. Chem. Soc. 1995, 117, 3734-3748). Other examples are jasplakinolide (J. Org. Chem. 1991, 56, 5196-5202) and other cytotoxic peptides (J. Org. Chem., 1989, 54, 617-627; Tetrahedron 1995, 51, 10653-10662; J. Org. Chem. 1989, 54, 736-738). The cyclosporin that has an immunosuppressive action also contains N-methyl-amino acids (see, for example, R. M. Wenger, Helv. Chim Acta 1983, 66, 2672-2702; S. L. Schreiber et al., Tetrahedron Lett. 1988, 29, 6577-6580). N-Methyl-amino acids can also have neuropharmacological activity (J. C. Watkins, J. Med. Pharm. Chem. 1962, 5, 1187-1199).

The incorporation of N-methyl-amino acids in biologically active peptides is often used, on the one hand, in pharmaceutical research to study conformation and biological activity (see, e.g., J. Org. Chem. 1981, 46, 3436-3440; Int. J. Pept. Protein Res 1995, 46, 47-55; Int. J. Pept. Protein Res. 1986, 27, 617-632). H. Kessler, Angew. Chem. [Applied Chemistry] 1982, 94, 509-520, and G. R. Marshall et al., Ann. Rep. Med. Chem. 1978, 13, 227-238 provide an overview on conformation studies of peptides and the connection with biological activity.

On the other hand, the substitution of amino acids in peptides by the corresponding N-methyl compounds is used to increase the activity or selectivity of the peptide ligands (see, e.g., J. Med. Chem. 1994, 37, 769-780; Int. J. Pept. Protein Res. 1995, 46, 47-55). N-Methyl-peptide bonds often show higher stability compared to proteolysis than the non-methylated bonds, which can result in an increased oral availability and extended action (R. H. Mazur et al., J. Med. Chem. 1980, 23, 758-763). Regarding the design of peptides by incorporation of N-methyl-amino acids and by other modifications, see W. F. Degrado, Adv. Protein Chem. 1988, 39, 51-124 and J. Rizo, L. M. Gierasch, Annu. Rev. Biochem 1993, 61, 387-418. For overviews regarding peptidomimetics, see A. Giannis et al., Angew. Chem. 1993, 105, 1303-1326 and J. Gante, Angew. Chem. 1994, 106, 1780-1802.

In WO 01/44177, a peptide that contains an N-methyl-homocysteine in a cyclic 6-mer partial sequence is described. The binding of a metal ion-binding sequence is carried out via the sulfur atom of the homocysteine. By the chelation of radionuclides such as $^{99m}$Tc or $^{186}$Re, use as radiodiagnostic agents or radiotherapeutic agents in the diagnosis or therapy of carcinoses is possible (see also U.S. Pat. Nos. 6,056,940, 6,022,857, 6,017,509).

The synthesis of the peptide is carried out in WO 01/44177 by N-methylation in the step-by-step course of the synthesis (see, e.g., J. Am. Chem. Soc. 1997, 119, 22301-2302). A 4-mer peptide, which is C-terminally bonded to a solid phase, is reacted with the amino acid N-Fmoc-S-tritylhomocysteine (Fmoc=9H-fluorene-9-ylmethyloxycarbonyl), which is accessible from methionine in three steps (J. Med. Chem. 1996, 39, 1361-1371) to form 5-mer peptide. After the protective group is cleaved off, the terminal amino group of the homocysteine is reacted with 2-nitrobenzenesulfonic acid chloride to form sulfonamide. The methylation with MTBD (1,3,4,6,7,8-hexahydro-1-methyl-2H-pyrimido [1,2-a]pyrimidene) and subsequently the cleavage of the sulfonyl group with 2-mercaptoethanol are then carried out. The peptide sequence is then further built up. This synthesis, however, has the drawback of an incomplete reaction and requires an additional purification of the peptide.

The creation of peptide sequences that contain N-methyl-amino acids is usually carried out by the reaction of a partial sequence with an Fmoc-protected N-methyl-amino acid (see, e.g., J. Med. Chem. 1996, 39, 1361-1371). The amino acid N-Fmoc-N-methyl-S-tritylmocysteine that is required for the peptide sequence in WO 01/44177 therefore could not previously be produced.

In the literature, a number of methods for producing N-methyl-amino acids, which usually start from the corresponding non-methylated amino acids that are commercially available in large amounts as chiral natural substances, are provided.

The first synthesis of non-racemic N-methyl-amino acids comes from F. Fischer. In this case, the N-tosyl derivatives of the amino acids are methylated by reaction with sodium hydroxide solution and methyl iodide. After that, the cleavage of the tosyl group is carried out with boiling hydrochloric acid (Ann. Chem. 1913, 398, 96-125; Ber. dt chem. Ges. 1915, 48, 360-378). It is described that partial racemization occurs with this method (A. H. Cook et al., J. Chem. Soc. 1949, 1022-1028).

Another method of Fischer is the reaction of 2-bromocarboxylic acids with methylamine (Ber dt. chem. Ges. 1916, 49, 1355-1366; for an application, also see A. H. Cook et al., J chem Soc. 1949, 1022-1028). In this case, partially racemized products are also produced (see P. Quitt et al., Helv. Chim Acta 1963, 46, 327-333). We could confirm this observation with a reaction of 2-bromo-4-methylsulfanyl-butanoic acid with methylamine. In the literature, the production of N-methyl-L-methionine is described with the diazotization of D-methionine with subsequent substitution by bromide under retention, followed by a substitution by methylamine under inversion (N. Izumiya, A. Nagamatsu, Kyushu. Mem. Med. Sci. 1953, 4, 1-16). The enantiomeric purity of the product was not determined. We could show that even with a diazotization method of Eliman that is described as mild (Synthesis 1999, 583-585), the reaction sequence proceeds with only 75% enantiomeric excess. This method therefore is not suitable for the production of enantiomer-pure N-methyl-homocysteines.

A method that is used very frequently is the direct alkylation according to Benoiton with sodium hydride and methyl iodide in THF or DMF (Can. J. Chem. 1973, 51, 1915-1919. Can J. Chem. 1977, 55, 906-910). This method is used with respect to the standard for the production of Z- and Boc-protected N-methyl-amino acids (see, e.g., Tetrahedron 1996, 51, 10653-10662, D. L. Boger et al., J. Am. Chem. Soc. 1999, 121, 6197-6205, H. Waldmann et al., Chem. Eur. J. 1999, 5, 227-236). The reaction of Boc-protected methionine amide with methylating agents, such as methyl iodide, in our case results in the methylation of the sulfur atom with the formation of sulfonium ions (see also S. J. F. Macdonald et al., J. Med. Chem. 1999, 64, 5166-5175). This method therefore cannot be used for the production of N-methyl-homocysteines.

There are a number of methods for the production of N-methyl-amino acids that start from amino acid esters. These include the selective reduction of N-formyl amino acid esters with borane (Tetrahedron Lett. 1982, 23, 3315-3318, J. Org. Chem. 1991, 56, 5196-5202) and the reaction of Schiff bases of amino acid esters with dimethyl sulfate or methyl triflate with subsequent hydrolysis (M. J. O'Donnell et al., Tetrahedron Lett. 1984, 25, 3651-3654). With the saponification of amino acid esters to form amino acids, however, partial racemization occurs (S. T. Cheung, N. L. Benoiton, Can. J. Chem, 1977, 55, 906-910). These methods therefore also are not suitable.

Amino acids can also be reacted in a reductive alkylation with an aldehyde. The Schiff base that is intermediately formed is reduced in situ in the presence of hydrogen and a catalyst (R. E. Bowman et al. J. Chem. Soc. 1950, 1342-1345 and 1346-1349) or with sodium borohydride (K. A. Schellenberg, J. Org. Chem. 1963, 28, 3259-3261). This method is performed both in solution (see, e.g., J. Org. Chem. 1996, 61, 3849-3862; J. Org Chem. 1995, 60, 6776-6784) and in solid phase (see, e.g., J. Org. Chem. 1996, 61, 6720-6722, Tetrahedron Lett. 1997, 38, 4943-4946, Bioorg Med. Chem. Lett. 1995, 5, 47-50). Di- and tripeptides were also already permethylated by Bowman according to this method (J. Chem. Soc. 1950, 1349-1351). A selective monomethylation with formaldehyde is not possible according to this method but rather results in mixtures that consist of unmethylated, monomethylated and dimethylated amino acid, which cannot be separated (Quitt et al., Helv. Chim Acta 1963, 46, 327-333; see also R. E. Bowman, H. H. Stroud, J. Chem. Soc. 1950, 1342-1345).

For the synthesis of Fmoc-protected N-methyl-amino acids, the method of Freidinger (J. Org. Chem. 1983, 48, 77-81) is very popular. This method consists of two stages: in the first step, an oxazolidinone is formed by reaction of the amino acid with formaldehyde, which then is reduced to the N-methyl compound in the second step by means of triethylsilane under acidic conditions. The reaction of Fmoc-L-methionine with formaldehyde to form oxazolidinone with a yield of 88% was described by Friedinger, but the reduction with triethylsilane to Fmoc-N-methyl-L-methionine is still incomplete even after five days and has only a 22% yield (J. Org. Chem. 1983, 48, 77-81).

The object of the invention was therefore to find compounds that are used for the creation of peptide sequences, which contain the N-methylated homocysteines, and to avoid the solid phase N-methylation, as well as a method for production thereof.

The object of the invention is achieved by the N-methyl-homocysteines, which can be both enantiomer-pure and racemic, of general formula I,

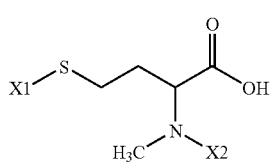

(I)

in which X1 stands for a sulfur protective group and X2 stands for a hydrogen atom or for a nitrogen protective group. X1 preferably stands for benzyl (Bn), 4-methoxybenzyl (Mob), diphenylmethyl, Bis(4-methoxyphenyl)methyl, 4,4'-dimethoxytriphenylmethyl (DMT), triphenylmethyl (trityl), methoxymethyl (MOM), 9H-fluorene-9-ylmethyl or tert-butylsulfide (T. W. Greene, P. G. M. Wuts, Protective Groups in Organic Synthesis, 2nd Edition, J. Wiley & Sons, New York 1991), preferably for benzyl (Bn), 4-methoxybenzyl (Mob), diphenylmethyl, bis(4-methoxyphenyl)methyl, 4,4'-dimethoxytriphenylmethyl (DMT) or triphenylmethyl (trityl), especially preferably for triphenylmethyl (trityl) and X2 in the case of a protective group preferably for 9H-fluorene-9-ylmethyloxycarbonyl (Fmoc), 2,7-dibromo-9H-fluorene-9-ylmethyloxycarbonyl, tert-butyloxycarbonyl (Boc), benzyloxycarbonyl (Cbz or Z), trifluoroacetyl, 2,2,2-trichloroethyloxycarbonyl (Troc), 2-trimethylsilylethyloxycarbonyl (Teoc) or 2-trimethylsilylethylsulfonyl (T. W. Greene, P. G. M. Wuts, see above), preferably for tert-butyloxycarbonyl (Boc), benzyloxycarbonyl (Cbz or Z) or 9H-fluorene-9-ylmethyloxy-carbonyl (Fmoc), especially preferably for 9H-fluorene-9-ylmethyloxycarbonyl (Fmoc).

The production of the compounds of general formula I according to the invention is carried out in that the oxazolidinone of formula II

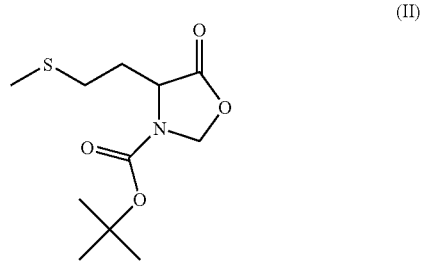

(II)

which is produced from methionine (see Example 1) according to literature methods (Ben-Ishai, J. Am. Chem. Soc. 1957, 79, 5736-5738; M. A. Blaskovich, M. Kahn, Synthesis 1998, 379-380; G. V. Reddy et al., Synth Commun 1999, 29, 4071-4077) is opened with a reducing agent in the presence of an acid to form the N-methylmethionine of formula III

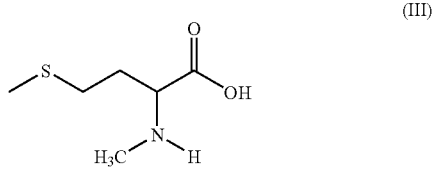

(III)

and then a sulfur protective group and optionally a nitrogen protective group are introduced in a way that is known in the art (see T. W. Greene, P. G. M. Wuts, see above). Alkylsilanes, preferably triethylsilane, are preferably used as reducing agents. Trifluoroacetic acid, pentafluoropropionic acid, trifluoromethanesulfonic acid or methanesulfonic acid, preferably trifluoroacetic acid, are preferably used as acids. The reaction is preferably carried out in chlorinated solvents, dioxane, THF, dimethoxyethane, preferably in dichloromethane or chloroform. The reaction is performed at a temperature of –20° C. to +100° C., preferably at 0 to 40° C. The reaction times are at five minutes up to ten hours, preferably 0.5 to 2 hours. N-Methylmethionine is obtained with yields of 70 to 95%.

The compounds of general formula I are used according to methods that are known to one skilled in the art (see M. Gooodman (editors), Houben-Weyl, Vol. E22, Synthesis of Peptides and Peptidomimetics. Thieme, 2001) for the creation of peptides and peptide intermediate stages that contain N-methyl-homocysteine, preferably for the production of Fmoc-(N-CH₃)Hcy(Trt)-Tyr(tBu)-D-Trp(Boc)-Lys(Boc)-Thr(tBu)-OH, cyclo-Tyr-D-Trp-Lys-Thr-Phe-(N—(CH₃) Hcy and cyclo-Tyr-D-Trp-Lys-Thr-Phe-(N—CH₃)Hcy (CH₂CO-â-Dap-Phe(4-NH₂)-Cys-Thr-Ser).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1 a) tert-Butyl-(S)-4-[2-(methylsulfanyl)ethyl)]-5-oxooxazolidinone-3-carboxylate A mixture of 100 g of N-(tert-butoxycarbonyl)-L-methionine (0.4 mol), 100 g of paraformaldehyde (3.3 mol), 200 g of dried magnesium sulfate (1.7 mol) and 4 g of paratoluenesulfonic acid (0.02 mol) in 1 l of toluene is heated for 3 hours to 90° C. It is allowed to cool to 20° C., and 800 ml of a saturated sodium bicarbonate solution is added to it while being cooled with ice. It is filtered off, and the residue is washed with 400 ml of ethyl acetate. The organic phase is extracted with 300 ml of water, dried on sodium sulfate and evaporated to the dry state in a vacuum. The crude product is dissolved in 150 ml of hexane/ethyl acetate 1:3 and filtered on silica gel, and the silica gel is rewashed with 500 ml of hexane/ethyl acetate 1:3. It is evaporated to the dry state in a vacuum, and 85.3 g (0.33 mmol, 83% of theory) of a yellow oil is obtained.

Cld.: C, 50.56; H, 7.33; N, 5.36; S, 12.27.
Fnd.: C, 50.38; H, 7.24; N, 5.43; S, 12.10.
IR: 2980,2920, 1800, 1715, 1390, 1170, 1050
NMR (CDCl₃): 1.5 (9H), 2.1 (3H), 2.15-2.35 (2H), 2.5-2.68 (2H), 4.33 (1H), 5.21 (1H), 5.48 (1H)
MS (EI): m/z 261, 205, 188, 116, 100, 57 b) N-Methyl-L-methionine 45 ml of trifluoroacetic acid and 40 ml of triethylsilane (0.25 mol) are added in drops at 0° C. to a solution of 19.4 g of tert-butyl-(S)4-[2-(methylsulfanyl)ethyl)]-5-oxooxazolidinone-3-carboxylate (0.074 mol) in 65 ml of dichloromethane at 0° C. It is stirred for one more hour while being cooled with ice and for one more hour at 20° C. Then, the reaction solution is evaporated to the dry state in a vacuum. The residue is again taken up three times with 100 ml of dichloromethane and again evaporated to the dry state. The residue is then taken up in 100 ml of water and extracted three times with 50 ml of MTBE. The water phase is evaporated to the dry state in a vacuum. The residue is again taken up three times with 50 ml of ethanol and again evaporated to the dry state. The residue is mixed with 150 ml of MTBE and stirred for 2 hours at 20° C. It is filtered off and rewashed with 50 ml of MTBE. After drying, 9.6 g (0.059 mol, 80% of theory) of a colorless solid is obtained.

Fnd.: C, 44.15; H, 8.03; N, 8.58; S, 19.64.
Cld.: C, 44.01; H, 7.83; N, 8.72; S, 19.80.
IR: 3440, 3010, 2920, 2830, 2420, 1735, 1675, 1580, 1205, 1140, 800, 720
NMR (DMSO): 2.01-2.08 (5H), 2.5-2.65 (5H), 3.74-3.78 (1H)
MS (FAB): m/z 164
CD (water): 200 nm, Δε1.64 c) N-Methyl-S-trityl-L-homocysteine 7.5 g (0.046 mol) of N-methyl-L-methionine is introduced, and 200 ml of ammonia is condensed while being cooled with MeOH/dry ice. At −35° C., 5.2 g (0.23 mol) of sodium is added in portions over one hour and stirred for two more hours. Then, 9.7 g (0.18 mol) of ammonium chloride is added in portions, the cooling is withdrawn, and the ammonia is driven off overnight with nitrogen. 14.0 g (0.054 mol) of triphenylmethanol is added. While being cooled with ice, 50 ml of dichloromethane and 90 ml of trifluoroacetic acid are then added. It is stirred for one hour at room temperature and evaporated to the dry state. The residue is suspended in 200 ml of water and brought to pH 13 with sodium hydroxide solution. After one more hour of stirring, it is suctioned off, and the solid is suspended in 500 ml of water. By adding citric acid, it is set at pH 4. 600 ml of MTBE is added and stirred for 30 minutes. It is suctioned off and washed twice with 100 ml each of MTBE. The residue is mixed with 100 ml of dichloromethane, 20 ml of ethanol is added, and then 500 ml of MTBE is added in drops. It is stirred for one more hour, suctioned off, washed with MTBE. After drying, 12.6 g (0.032 mol, 70% of theory) of a colorless solid is obtained.

Cld.: C, 73.62; H, 6.44; N, 3.58; S, 8.19.
Fnd.: C, 73.40; H, 6.30; N, 3.71; S, 8.02.
IR: 3440, 3055, 2850, 2400, 1615, 1485, 1445, 1395, 740, 700
NMR (CDCl₃): 1.28-1.62 (2H), 2.12 (3H), 2.25-2.45 (2H), 2.84-2.92 (1H), 7.12-7.41 (15H)
MS (EI), m/z 243, 165 d) N-(9H-Fluorene-9-ylmethyloxycarbonyl)-N-methyl-S-trityl-L-homocysteine 16.6 g (0.042 mol) of N-methyl-S-trityl-L-homocysteine is suspended in 90 ml of water and 100 ml of THF, and 12.58 g (0.12 mol) of sodium carbonate is added. At 10° C., 14.88 g (0.044 mol) of fluorenylmethylsuccinimidylcarbonate in 50 ml of THF is added in drops and stirred for three more hours. Then, it is mixed with 80 ml of water and 130 ml of ethyl acetate, stirred for ten minutes, and brought to pH 4 with citric acid. The organic phase is washed twice with 100 ml each of water and once with 100 ml of common salt solution. The aqueous phases are subsequently re-extracted once with 100 ml of ethyl acetate. The combined organic phase is concentrated by evaporation in a rotary evaporator, mixed with 260 ml of ethyl acetate and concentrated by evaporation in a rotary evaporator to 29.2 g of foam, which is chromatographed with dichloromethane/acetone 6:4. 22.4 g (0.036 mol, 86% of theory) of product is obtained.

Cld.: C, 76.32; H, 5.75; N, 2.28; S, 5.22.
Fnd.: C, 76.11; H, 5.52; N, 2.40; S, 5.38.
IR: 3430, 3060, 2950, 1740, 1710, 1175, 740, 700
NMR (CDCl13): 1.46-2.35 (4H),2.66-2.73 (3H), 4.13-4.6 (4H), 7.13-7.79 (23H)
MS (FAB): m/z 614, 636

EXAMPLE 2

The enantiomeric compound in the title compound of Example 1d can be obtained analogously if, as described above, N-(tert-butoxycarbonyl)-D-methionine is used instead of N-(tert-butoxycarbonyl)-L-methionine.

a) tert-Butyl-(R)-4-[2-(methylsulfanyl)ethyl)]-5-oxooxazolidinone-3-carboxylate

Cld.: C, 50.56; H, 7.33; N, 5.36; S, 12.27.
Fnd.: C, 50.30; H, 7.51; N, 5.50; S, 12.41.
IR: 2980, 2920, 1800, 1715, 1390, 1175, 1050
NMR (CDCl3): 1.5 (9H), 2.08 (3H), 2.15-2.35 (2H), 2.5-2.68 (2H), 4.33 (1H), 5.21 (1H), 5.48 (1H)
MS (El): m/z 261, 205, 188, 116, 100, 57 b) N-Methyl-D-methionine

Cld.: C, 44.15; H, 8.03; N, 8.58; S, 19.64.
Fnd.: C, 43.98; H, 7.81; N, 8.70; S, 19.82.
IR: 3430, 3010, 2920, 2830, 2420, 1630, 1580, 1395
NMR (D2O): 2.13 (3H), 2.12-2.22 (2H), 2.55-2.68 (2H), 2.74 (3H), 3.68-3.73 (1H)
MS (EI): m/z 163, 145, 118, 88, 70, 61
CD (water): 200 nm, å 1.87 c) N-Methyl-S-trityl-D-homocysteine

Cld.: C, 73.62; H, 6.44; N, 3.58; S, 8.19.
Fnd.: C, 73.45; H, 6.25; N, 3.78; S, 8.15.
IR: 3440, 3055, 2850, 2400, 1615, 1485, 1445, 1395, 740, 700
NMR (CDCl3): 1.28-1.62 (2H), 2.12 (3H), 2.25-2.45 (2H), 2.84-2.92 (1H), 7.12-7.41 (15H)
MS (El); m/z 243, 165 d) N-(9H-Fluorene-9-ylmethyloxycarbonyl)-N-methyl-S-trityl-D-homocysteine

Cld.: C, 76.32; H, 5.75; N, 2.28; S, 5.22.
Fnd.: C, 76.15; H, 6.58; N, 2.41; S, 5.30.
IR: 3440, 3055, 2950, 2600, 1740, 1705, 1445, 1170, 740, 700
NMR (CDCl3): 1.45-2.35 (4H), 2.65-2.73 (3H), 4.14-4.62 (4H), 7.13-7.81 (23H)
MS (FAB): m/z 636, 614

EXAMPLE 3

N-Benzyloxycarbonyl-N-methyl-S-trityl-L-homocysteine 16.6 g (0.042 mol) of N-methyl-S-trityl-L-homocysteine (title compound of Example 1c) is suspended in 90 ml of water and 100 ml of THF, and 12.58 g (0.12 mol) of sodium carbonate is added. At 10° C., 10.97 g (0.044 mol) of N-benzyloxycarbonyl-oxysuccinimide, dissolved in 50 ml of THF, is added in drops and stirred for three more hours at 10° C. Then, it is mixed with 80 ml of water and 130 ml of ethyl acetate, stirred for ten minutes at room temperature and brought to pH 4 with citric acid. The organic phase is washed twice with 100 ml each of water and once with 100 ml of common salt solution. The aqueous phases are subsequently re-extracted once with 100 ml of ethyl acetate. The combined organic phases are evaporated to the dry state in a vacuum; the residue is chromatographed on silica gel (mobile solvent: dichloromethane/acetone 6:4). 22.08 g (87% of theory) of product is obtained as a solid, colorless foam.

Elementary analysis:
Cld.: C, 73.12; H, 5.94; N, 2.66; S, 6.10.
Fnd.: C, 72.87; H, 6.08; N, 2.60; S, 5.98.

EXAMPLE 4

N-tert-Butyloxycarbonyl-N-methyl-S-trityl-L-homocysteine 16.6 g (0.042 mol) of N-methyl-S-trityl-L-homocysteine (title compound of Example 1c) is suspended in 90 ml of water and 100 ml of THF, and 12.58 g (0.12 mol) of sodium carbonate is added. At 10° C., 9.60 g (0.044 mol) of Di-tert-butyl-dicarbonate, dissolved in 50 ml of THF, is added in drops and stirred for three more hours at 10° C. Then, it is mixed with 80 ml of water and 130 ml of ethyl acetate, stirred for ten minutes at room temperature and brought to pH 4 with citric acid. The organic phase is washed twice with 100 ml each of water and once with 100 ml of common salt solution. The aqueous phases are subsequently re-extracted once with 100 ml of ethyl acetate. The combined organic phases are evaporated to the dry state in a vacuum, the residue is chromatographed on silica gel (mobile solvent: dichloromethane/acetone 6:4). 17.14 g (83% of theory) of a product is obtained as a solid, colorless foam.

Elementary analysis:
Cld.: C, 70.85; H, 6.77; N, 2.85; S, 6.52.
Fnd.: C, 70.68; H, 6.91; N, 2.74; S, 6.42.

EXAMPLE 5 a) N-Methyl-S-(4,4'-dimethoxy-trityl)-L-homocysteine 7.5 g (0.046 mol) of N-methyl-L-methionine (title compound of Example 1b) is introduced, and 200 ml of ammonia is condensed while being cooled with MeOH/dry ice. At −35° C., 5.2 g (0.23 mol) of sodium is added in portions over one hour and stirred for two more hours. Then, 9.7 g (0.18 mol) of ammonium chloride is added in portions, the cooling is withdrawn, and the ammonia is driven off overnight with nitrogen. 17.3 g (0.054 mol) of bis(4-methoxyphenyl)-phenyl-methanol (DMT) is added. While being cooled with ice, 50 ml of dichloromethane and 90 ml of trifluoroacetic acid are then added. It is stirred for one hour at room temperature and evaporated to the dry state. The residue is suspended in 200 ml of water and brought to pH 13 with sodium hydroxide solution. After one more hour of stirring, it is suctioned off, and the solid is suspended in 500 ml of water. By adding citric acid, it is set at pH 4. 600 ml of MTBE is added and stirred for 30 minutes. It is suctioned off and washed twice with 100 ml each of MTBE. The residue is mixed with 100 ml of dichloromethane, 20 ml of ethanol is added, and then 500 ml of MTBE is added in drops. It is stirred for one more hour, suctioned off, washed with MTBE. After drying, 13.92 g (67% of theory) of a colorless solid is obtained.

Elementary analysis:
Cld.: C, 69.15; H, 6.47; N, 3.10; S, 7.10.
Fnd.: C, 68.98; H, 6.63; N, 3.01; S, 7.02.

b) N-(9H-Fluorene-9-ylmethyloxycarbonyl)-N-methyl-S-(4,4'-dimethoxytrityl)-L-homocysteine 18.97 g (0.042 mol) of N-methyl-S-4,4'-dimethoxytrityl-L-homocysteine (title compound of Example 5a) is suspended in 90 ml of water and 100 ml of THF, and 12.58 g (0.12 mol) of sodium carbonate is added. At 10° C., 14.88 g (0.044 mol) of fluorenylmethylsuccinimidiyl carbonate, dissolved in 50 ml of THF, is added in drops, and it is stirred for three more hours at 10° C. Then, it is mixed with 80 ml of water and 130 ml of ethyl acetate, stirred for ten minutes at room temperature and brought to pH 4 with citric acid. The organic phase is washed twice with 100 ml each of water and once with 100 ml of common salt solution. The aqueous phases are subsequently re-extracted once with 100 ml of ethyl acetate. The combined organic phases are evaporated to the dry state in a vacuum; the residue is chromatographed on silica gel (mobile solvent: dichloromethane/acetone 6:4). 22.92 g (81% of theory) of product is obtained as a solid, colorless foam.

Elementary analysis:

Cld.: C, 73.08; H, 5.83; N, 2.08; S, 4.76.

Fnd.: C, 72.95; H, 5.94; N, 2.01; S, 4.68.

EXAMPLE 6

Fmoc-(N—CH$_3$)Hcy(Trt)-Tyr(tBu)-D-Trp(Boc)-Lys(Boc)-Thr(tBu)-ClTrt-Solid Phase

The peptide Fmoc-Tyr(tBu)-D-Trp(Boc)-Lys(Boc)-Thr(tBu)-ClTrt solid phase substrated on solid phases produced as described in WO 01/44177 (Example 1, steps 1-3) was treated with 5% piperidine in 1:1 NMP/DCM (75 ml) for 10 minutes followed by a reaction with 20% piperidine in NMP (75 ml) for 15 minutes. The solid phase was washed in succession with NMP (3×75 ml×1 minute) and DCM (3×75 ml×1 minute). A ninhydrin analysis performed on a small sample of the solid phase showed the end of the reaction, and the solid phase was washed with NMP (75 ml). A small portion of the carrier resin was treated with HFIPA and analyzed by HPLC (see HPLC Method 1 from Diatide). The peak for Fmoc-Tyr(tBu)-D-Trp(Boc)-Lys(Boc)-Thr(tBu)-OH at 21.7 minutes was not detected, but a peak at 12.7 minutes for H-Tyr(tBu)-D-Trp(Boc)-Lys(Boc)-Thr(tBu)-OH was detected. In a separate container, N-á-Fmoc-N-á-methyl-S-trityl-homocysteines (9.20 g, 15 mmol), HATU reagent (5.70 g, 15 mmol) and HOAt (2.04 g, 15 mmol) in 50 ml of NMP were dissolved. DIEA (6.96 ml, 40 mmol) was added to the solution of the protected N-methylhomocysteine. It was stirred for one minute, and the mixture was added to the solid-phase batch. The reaction was shaken for 4 hours under a light argon stream. The solution was separated, and the solid phases were washed in succession with NMP (3×75 ml×1 minute) and DCM (3×75 ml×1 minute). A ninhydrin analysis performed on a small sample of the solid phase showed the end of the reaction. A smaller portion of the carrier resin was treated with HFIPA and analyzed by HPLC (see HPLC Method I with diatides). The peak for H-Tyr(tBu)-D-Trp(Boc)-Lys(Boc)-Thr(tBu)-OH at 12.7 minutes was not detected, but a peak at 26.7 minutes for Fmoc-(N-CH$_3$)Hcy(Trt)-Tyr(tBu)-D-Trp(Boc)-Lys-(Boc)-Thr(tBu) OH was detected.

The entire disclosures of all applications, patents and publications, cited herein and of corresponding German application No. 102 15 336.1, filed Mar. 28, 2002, and U.S. Provisional Application Ser. No. 60/331,416, filed Nov. 15, 2001 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. Compounds of general formula I

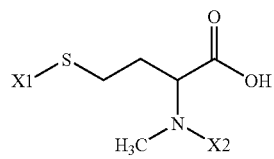

in which

X1 stands for a sulfur protective group, and

X2 stands for a hydrogen atom or for a nitrogen protective group.

2. Compounds according to claim 1, wherein

X1 stands for benzyl (Bn), 4-methoxybenzyl (Mob), diphenylmethyl, bis(4-methoxyphenyl)methyl, 4,4'-dimethoxytriphenylmethyl (DMT), triphenylmethyl (trityl), methoxymethyl (MOM), 9H-fluorene-9-ylmethyl or tert-butylsulfide.

3. Compounds according to claim 1, wherein

X2 stands for 9H-fluorene-9-ylmethyloxycarbonyl (Fmoc), 2,7-dibromo-9H-fluorene-9-ylmethyloxycarbonyl, tert-butyloxycarbonyl (Boc), benzyl oxycarbonyl (Cbz or Z), trifluoroacetyl, 2,2,2-trichloroethyloxycarbonyl (Troc), 2-trimethylsilylethyloxy-carbonyl (Teoc) or 2-trimethylsilylethylsulfonyl.

4. A process for preparing a compound of formula I according to claim 1, comprising reacting the oxazolidone of formula II

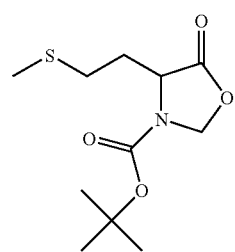

with a reducing agent in the presence of an acid to form the N-methylmethionine of formula III

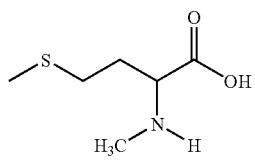

and then introducing a sulfur protective group and a nitrogen protective group.

5. A process according to claim 4, wherein the reducing agent is an alkylsilane.

6. A process according to claim 4, wherein as acid is trifluoroacetic acid, pentafluoropropionic acid, trifluoromethylsulfonic acid or methanesulfonic acid.

7. In a process for preparing a peptide or peptide intermediate that contains N-methyl-homocysteine, the improvement comprising using a compound according to claim 1 as an intermediate.

8. A process according to claim 7, wherein Fmoc-(N—CH$_3$)Hcy(Trt)-Tyr(tBu)-D-Trp(Boc)-Lys(Boc)-Thr(tBu)-OH is prepared.

9. A process according to claim 7, wherein cyclo-Tyr-D-Trp-Lys-Thr-Phe-(N—CH$_3$)Hcy is prepared.

10. A process according to claim 7, wherein cyclo-Tyr-D-Trp-Lys-Thr-Phe-(N—CH$_3$)Hcy(CH$_2$CO-β-Dap-Phe(4-NH$_2$)-Cys-Thr-Ser) is prepared.

11. A process according to claim 7, which avoids solid phase N-methylation of homocysteine.

12. A compound according to claim 1, wherein X1 stands for 4-methoxybenzyl (Mob), diphenylmethyl, bis(4-methoxyphenyl)methyl, 4,4'-dimethoxytriphenylmethyl (DMT), triphenylmethyl (trityl), methoxymethyl (MOM), 9H-fluoren-9-ylmethyl or tert-butylsulfide.

13. A compound of formula I

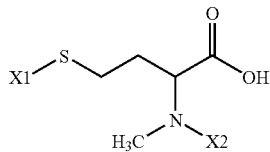

in which
X1 stands for benzyl (Bn), 4-methoxybenzyl (Mob), diphenylmethyl, bis(4-methoxyphenyl)methyl, 4,4'-dimethoxytriphenylmethyl (DMT), triphenylmethyl (trityl), methoxymethyl (MOM), 9H-fluoren-9-ylmethyl or tert-butylsulfide, and
X2 stands for 9H-fluoren-9-ylmethyloxycarbonyl (Fmoc), 2,7-dibromo-9H-fluoren-9-ylmethyloxycarbonyl, tert-butyloxycarbonyl (Boc), benzyl oxycarbonyl (Cbz or Z), trifluoroacetyl, 2,2,2-trichloroethyloxycarbonyl (Troc), 2-trimethylsilylethyloxycarbonyl (Teoc) or 2-trimethylsilylethylsulfonyl.

14. A compound according to claim 13, wherein X1 stands for 4-methoxybenzyl (Mob), diphenylmethyl, bis(4-methoxyphenyl)methyl, 4,4'-dimethoxytriphenylmethyl (DMT), triphenylmethyl (trityl), methoxymethyl (MOM), 9H-fluoren-9-ylmethyl or tert-butylsulfide.

15. A process for preparing a compound of formula I according to claim 1, comprising reacting the oxazolidinone of formula II

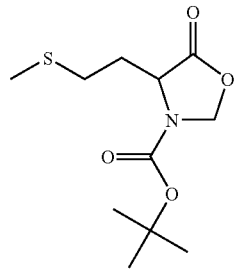

with a reducing agent in the presence of an acid to form the N-methylmethionine of formula III

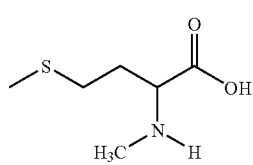

and then introducing a sulfur protective group X1 and a nitrogen protective group X2, to form a compound of formula I

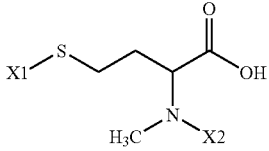

in which
X1 stands for a sulfur protective group, and
X2 stands for a nitrogen protective group.

16. A process according to claim 15, wherein the reducing agent is an alkylsilane.

17. A process according to claim 15, wherein the acid is trifluoroacetic acid, pentafluoropropionic acid, trifluoromethylsulfonic acid or methanesulfonic acid.

* * * * *